United States Patent [19]
Kadir et al.

[11] Patent Number: 5,945,378
[45] Date of Patent: Aug. 31, 1999

[54] CONTROL OF CYPERUS SPP. WITH A FUNGAL PATHOGEN

[75] Inventors: Jugah Kadir; Raghavan Charudattan, both of Gainsville, Fla.

[73] Assignee: University of Florida, Gainesville, Fla.

[21] Appl. No.: 08/899,020

[22] Filed: Jul. 23, 1997

Related U.S. Application Data

[63] Continuation-in-part of application No. 08/703,082, Aug. 26, 1996, Pat. No. 5,698,491.

[51] Int. Cl.$^6$ .................................................. A01N 63/04
[52] U.S. Cl. ................................................................ 504/117
[58] Field of Search ............................................. 504/117

[56] References Cited

U.S. PATENT DOCUMENTS

| | | | |
|---|---|---|---|
| 3,849,104 | 11/1974 | Daniel et al. | 71/65 |
| 3,999,973 | 12/1976 | Templeton | 71/79 |
| 4,162,912 | 7/1979 | Charudattan | 71/79 |
| 4,626,271 | 12/1986 | Gleason | 71/66 |
| 4,731,104 | 3/1988 | Phatak et al. | 71/79 |
| 4,915,726 | 4/1990 | Bewick et al | 71/79 |
| 5,256,627 | 10/1993 | Bewick | 504/117 |
| 5,434,121 | 7/1995 | Gohbara et al. | 504/117 |

FOREIGN PATENT DOCUMENTS

| | | |
|---|---|---|
| 0207653 | 1/1987 | European Pat. Off. . |

OTHER PUBLICATIONS

Kadir, J. and R. Charudattan (1996) "*Dactylaria higginsii* (Luttrell) M.B. Ellis: A Potential Bioherbicide for Nutsedges (*Cyperus* spp)" WSSA Abstracts No. 159, vol. 36, p. 49, 1996 Meeting of the Weed Science Society of America (Feb. 5–8, 1996).

Evans, Harry C. (1995) "Fungi as biocontrol agents of weeds: a tropical perspective" Can. J. Bot. 73(Suppl. 1):S58–S64.

Kadir, J.B. R. Charudattan, R.D. Berger, W.M. Stall, B.J. Brecke (1997) "Field efficacy of Dactylaria higginsii for control of purple nutsedge" Phytopathology 87(6):S49 (XP002045134) abstract only.

Hashioka, Y. (1973) "Notes on Pyricularia. II. Four species and one variety parasitic to Cyperaceae, Gramineae and Commelinaceae" XP002045130, published in Transactions of the Mycological Society of Japan, 14(3):256–265. (abstract only).

Nitzani, E., R. Kenneth, Y. Kleifield, Reuveni R. Rehovot, Isr Haifa (1990) "Foliar Diseases of Purple Nutsedge (Cyperus rotundus) in Israel, as Potential Biocontrol Agents" Phytoparasitica 18(3):240–241 (XP002045131) abstract only.

Kadir, J.B., R. Charudattan, W.M. Stall, T.A. Bewick (1997) "Effect of Dactylaria higginsii on the interference of purple nutsedge with tomato and pepper" Phytopathology 87(6):S50(XP002045135) abstract only.

Nitzani, E. Bonne, R.G. Kenneth, Y. Kleifeld, Rehovot R. Reuveni, Haifa Post (1988) "Fungal Diseases of the Noxious Weed Cyperus rotundus in Israel" Phytoparasitica 16(1):70–71, (XP002045132) abstract only.

(List continued on next page.)

*Primary Examiner*—S. Mark Clardy
*Attorney, Agent, or Firm*—Saliwanchik, Lloyd & Saliwanchik

[57] ABSTRACT

The subject invention concerns a novel bioherbicide and its use to control weeds known as nutsedges(Cyperus spp.). The novel fungus, *Dactylaria higginsii* (Luttrell) M. B. Ellis is pathogenic to purple nutsedge, yellow nutsedge, annual sedge, globe sedge, rice flatsedge, and *Cyperus brevifolius*. These sedges cause major losses in different crops and turf. Accordingly, the fungus of the subject invention is an important advance in the control of these noxious weeds.

3 Claims, 4 Drawing Sheets

OTHER PUBLICATIONS

Bareto, R.W., H.C. Evans (1995) "Mycobiota of the weed Cyperus rotundus in the state of Rio de Janeiro, with an elucidation of its associated Puccinia complex" Mycological Research 99(4):407–419 (XP002045133) abstract only.

Fleming, Malcolm H. (1987) "Agricultural chemicals in ground water: Preventing contamination by removing bariers against low–input farm management" Amer. J. Alternative Agriculture II(3):124–130.

Holm, L.G. et al. (1977) The World's Worst Weeds: Distribution and Biology, University Press of Hawaii pp. 8–24; 125–133; and 236–243.

McWhorter, C.G. (1984) "Future Needs in Weed Science" Weed Science 32:850–855.

Pereira, W. et al. (1987) "Herbicide Action on Purple and Yellow Nutsedge (*Cyperus rotundus* and *C. esculentus*" Weed Technolgy 1:92–98.

Phatak, S.C. et al. (1987) "Biological Control and Its Integration in Weed Management Systems for Purple and Yellow Nutsedge (*Cyperus rotundus* and *C. esculentus*)" Weed Technology 1:84–91.

A. 0.05% N-Gel + conidia
B. 0.02% Silwet L-77 + conidia
C. Control, water only
D. Control, conidia in water
E. 0.05% Metamucil + conidia
  (conidia = $10^6$ per ml.)

CONTROL OF CYPERUS SPP. WITH A FUNGAL PATHOGEN

CROSS-REFERENCE TO A RELATED APPLICATION

The subject application is a continuation-in-part of application Ser. No. 08/703,082, filed on Aug. 26, 1996, now U.S. Pat. No. 5,698,491.

The subject invention was made with government support under a research project supported by USDA Special Grants Program: CBAG Grant No. 94-34135-0649. The government has certain rights in this invention.

BACKGROUND OF THE INVENTION

Weeds are a tremendous problem for farmers and growers throughout the world. It has been estimated that weeds cause a 10–12% loss of value ($20 billion annually) for agricultural products in the United States (McWhorter, C. G. [1984] *WeedSci.* 32:850–855). In Florida, losses due to weeds are estimated to be over $100 million per year from vegetable production, alone. About 41% of the cost of plant protection has been estimated to be for the control of weeds. Herbicides are applied to more acres than fungicides and insecticides combined. Weeds act as alternate hosts for insects, fungi, bacteria, and viruses. They affect man, not only by competing with crop plants, but by poisoning range animals, interfering with right-of-waysand roadways, decreasing forest production, and marring landscapes. A particularly notable class of weed is nutsedge.

Nutsedges (Cyperus spp.) comprise a group of commonly occurring weeds that are among the most difficult to control. In the United States and the Caribbean Basin there are three species which are of most consequence, namely *C. rotundus* (purple nutsedge), *C. exculentus* (yellow nutsedge), and *C. iria* (rice flatsedge). Together, these nutsedge species are problematic for virtually every crop grown in Florida. Yield reduction due to nutsedge varies. In agronomic crops, e.g., in maize, yield reduction can be as high as 79%. In horticultural crops, yield reductions can reach 80%. Vegetables, particularly tomato, pumpkin, pepper, and onion, can be affected. Yield reduction in tomato, a very valuable crop in the United States, can be as high as 53%. Nutsedges cannot compete with crops if a dense crop canopy is established, making early season control of these weeds essential.

Purple nutsedge has been called the world's worst weed because of its distribution worldwide and its resistance to control measures (Holm, L. G., D. L. Plucknett, J. V. Pancho, and J. P. Herberger [1977] *The World's Worst Weeds: Distribution and Biology*. University Press of Hawaii, Honolulu). It is a problem in 52 crops in more than 90 tropical and subtropical countries. It is considered a serious weed in the United States, especially in the warm regions of the southern states from North Carolina to California. It is also considered a principal weed in Puerto Rico.

Yellow nutsedge is more tolerant of cold and drought than purple nutsedge and, therefore, is found over a wider geographic area. It survives as an important weed as far north as Canada and Alaska. Worldwide, yellow nutsedge is not as aggressive and important a weed as purple nutsedge, although, it is a weed of importance in 21 crops in nearly 40 countries of the world and is a serious or principal weed in 15 countries. Yellow nutsedge is a serious or principal weed of sugarcane, maize, potato, cotton, and soybean, chiefly in southern Africa and North America. In some countries, it is listed as one of the three most serious weeds of sugarcane, corn, and potato.

In North America, yellow nutsedge is found in Nova Scotia, New Brunswick, Quebec, Ontario, Manitoba, Alaska, and all of the contiguous United States except North Dakota. It is a principal weed of sugarbeet and vegetables and is an important weed of maize, potato, soybean, and cotton. In Hawaii, it is found as a principal weed of sugarcane. Yellow nutsedge was one of the most troublesome and costly weeds in the southeastern United States. In cotton production, it ranked as the fifth most important weed.

The weed *Kyllinga brevifolia* (=*Cyperus brevifolius*) is an important weed in turfgrass, golf courses, and other situations. Kyllinga is difficult to control with existing chemical herbicides.

Many herbicides have been tested for control of purple and yellow nutsedge. Pereira et al. recently reviewed this research (Pereira, W., G. Crabtree, R. D. William [1987] *Weed Technology* 1:92–98). Herbicides based on virtually every mode of action have been studied. Examples are: 2, 4-D ("control erratic"), atrazine ("control inconsistent"), linuron ("marginal control"), paraquat ("inconsistent"), alachlor and metolachlor ("control temporary"). Some herbicides that have been used successfully include glyphosate, dichlobenil, EPTC, arsenicals, and soil flumigants. Success or failure of a herbicide treatment depends on such factors as nutsedge growth stage at application, soil moisture and temperature, and addition of adjuvants to the spray mixture.

Chemical weed control programs are seriously inadequate for control of nutsedges. Frequently, the weed germinates below the treated zone and avoids herbicide injury. Although many herbicides have been developed and tested in the last three decades, farmers still rely heavily on dinoseb, a herbicide developed in the 1950s. Dinoseb is a contact herbicide that causes injury to some field crops. Alternative approaches include monosodium methanearsonate (MSMA), paraquat, toxaphene, and triazine herbicides, but these chemicals are not registered for use on some crops or have been banned altogether in certain countries for reasons of toxicology and/or crop safety.

The use of chemical pesticides in agriculture is currently a major concern in the U.S. Nowhere is this concern more obvious than in the San Joaquin Valley of Calif., where pesticides are being blamed for an epidemic of cancer in children and young adults (Weisskopf, M. [1988] *The Washington Post Weekly Edition* 5(47):10–11, Washington, D.C.). New technologies in detection methods are enabling researchers to find pesticides in the environment that were previously thought to be totally degraded. One major public concern is protection of groundwater. The Environmental Protection Agency (EPA) estimates that 100,000 of the nation's 1.3 million wells are contaminated with pesticides (Fleming, M. H. [1987] *Amer. J Alternative Agriculture* 2:124–130). This has alarmed the general public since 50% of all Americans depend on groundwaterwells for their fresh water supplies. Because herbicides are so widely used in agriculture, and because they are often applied directly to the soil, the potential for movement into groundwater by leaching is perhaps greater than any other pesticide. Other inadequacies of chemical controls include lack of residual control, injury to non-target organisms, undesirable residues in harvested products, and carryover in subsequent crops.

There are no selective herbicides which can be used to control sedges in all crops. Indeed, those herbicides which are available do not always give acceptable control of these weeds. An alternative is offered by the use of microbes which have herbicidal activity specific for the problem weeds, and do not infect desirable plants.

Phatak et al. (Phatak, S. C., M. B. Callaway, C. S. Vavrina [1987] *Weed Technology* 1:84–91) have reviewed biological control of purple and yellow nutsedge. Cost effective procedures for the use of insects to control these species have not been developed. Phatak has reported that manipulation of a rust pathogen (*Puccinia canaliculata*) of yellow nutsedge has reduced stand, tuber formation, and completely inhibited flower formation of this weed. Phatak points out that little research has been directed toward integrating biological and chemical control of nutsedge. It was shown that rust-paraquat (1,1'-dimethyl-4,4'-bipyridinium ion) combinations were much more effective than either treatment alone. Other work indicates that sequential applications of the rust and other herbicides, such as bentazon [3-(1-methylethyl)-(1H)-2,1,3-benzothiadiazin-4-(3H)-one 2,2-dioxide] provided significantly better control than either applied alone. Although this system is promising, there are many aspects that must be investigated, such as spore production and maintenance in storage. Phatak also states that other pathogens should be sought to complement the rust system.

Therefore, the use of bioherbicides is becoming an increasingly important alternative to chemical herbicides. This importance is exemplified by several patents which have been issued for bioherbicides and their use. Some of these patents, by way of illustration, are as follows: U.S. Pat. No. 3,849,104 (control of northern jointvetch with *Colletotrichum gloeosporioides* Penz. *aeschynomene*); U.S. Pat. No. 3,999,973 (control of prickly sida [teaweed] and other weeds with *Colletotrichum malvarum*); U.S. Pat. No. 4,162,912 (control of milkweed vine with *Araujia mosaic* virus); U.S. Pat. No. 4,626,271 (cyanobacterin herbicide); U.S. Pat. No. 4,915,726 (biological control of dodder); U.S. Pat. No. 5,256,627 (control of nutsedge using Curvularia and Fusarium fungi).

BRIEF SUMMARY OF THE INVENTION

The subject invention concerns a novel means for producing and delivering a toxin. Advantageously, the toxin produced according to the subject invention has been shown to have phytotoxic properties. The toxin is produced from a novel fungal isolate. This novel isolate, *Dactylaria higginsii* (Luttrell) M. B. Ellis, can be grown, and the toxins recovered, by techniques which are well known to those skilled in the art having the benefit of the instant disclosure.

Furthermore, it has been discovered that this fungus can be used to directly and specifically deliver its phytotoxin composition to sedges (Cyperus spp.). Thus, in a preferred embodiment, the subject invention concerns the discovery of a novel method for control of sedges. This method has been shown to have surprising ability to provide specific control of both yellow and purple nutsedge. In this preferred embodiment, the phytotoxin composition of the subject invention is delivered to the sedge by applying an effective amount of the biologically-active fungus directly to the plant. The fungus produces sufficient quantities of a phytotoxic compound to inhibit the growth, or actually induce mortality, of the target weed. The growth of the fungus can also mechanically disrupt nutrient transport in the vascular system of the target weed.

The subject invention further concerns the novel microbe itself, which is effective when used according to the methods disclosed herein, in controlling sedges without adversely affecting the growth and yield of desired field crops. Preferably, the subject invention relates to the use of a composition comprising spores from *Dactylaria higginsii* (Luttrell) M. B. Ellis in association with an agricultural carrier wherein said spores are in a concentration of from about $1 \times 10^4$ spores/ml of carrier to about $1 \times 10^9$ spores/ml of carrier. The concentrated spore formulation can be adapted for distribution over geographical locales or situs where the spores germinate and infect sedges (Cyperus spp.), including yellow or purple nutsedge, and rice flatsedge.

The fungal isolate of the subject invention can also be used to control *Kyllinga brevzfolia* (=*Cyperus brevifolius*).

DETAILED DISCLOSURE OF THE INVENTION

Figure 1:
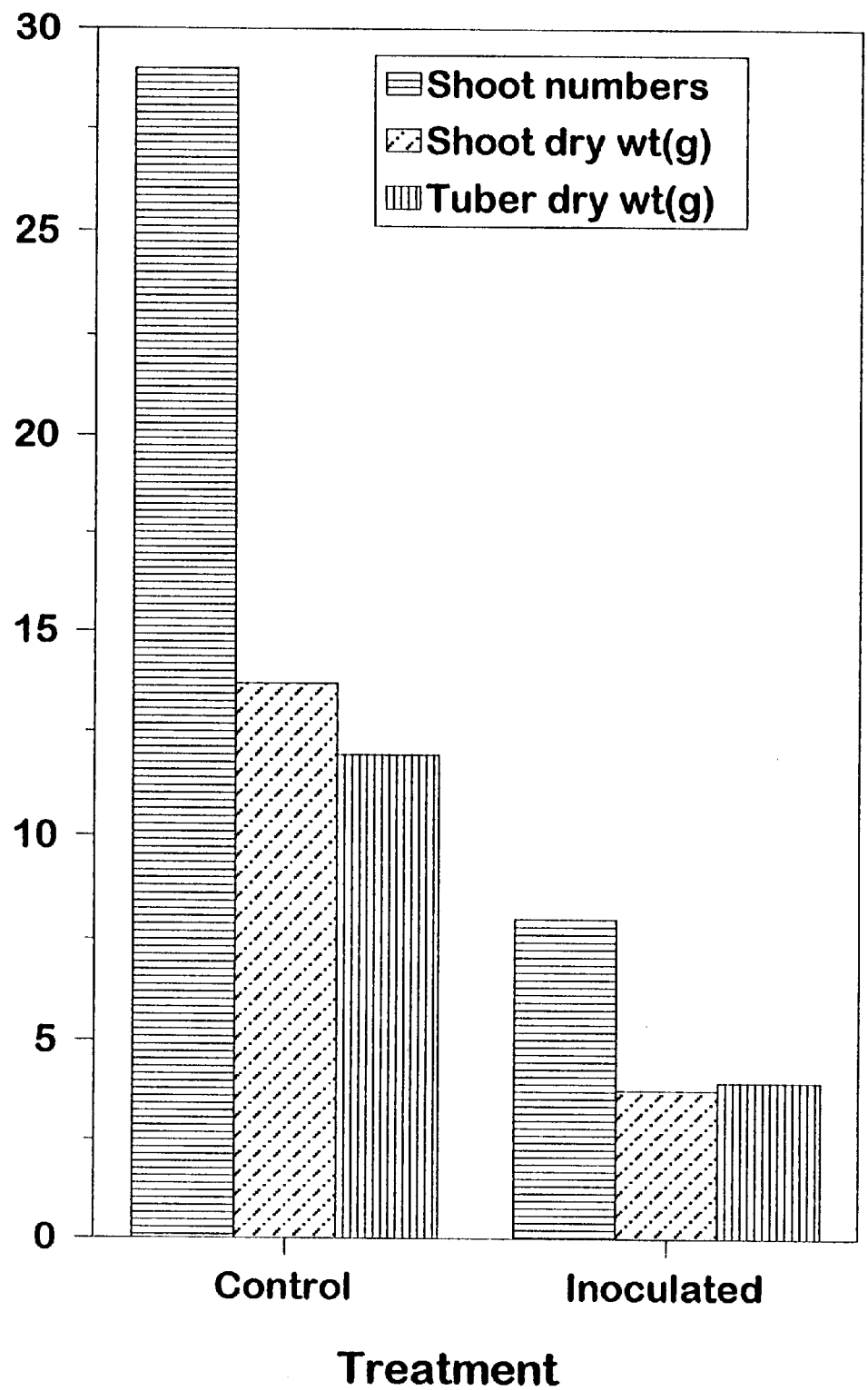
FIG. 1 shows the effect of inoculation of *D. higginsii* on the growth of purple nutsedge.

The subject invention provides a novel means of obtaining and using a toxin composition. This toxin composition is obtained from a novel fungal isolate. Advantageously, the toxin produced by this fungal isolate has activity against weeds of the Cyperus genus, which are referred to herein as "sedges" and are known to be particularly difficult to control. The toxins of the subject invention may also be purified and used against other weeds. For purposes of this application, a "weed" is any plant that is objectionable or interferes with the activities or welfare of man.

One highly useful aspect of the novel fungal isolate described herein is its unique and surprising ability to effectively and selectively deliver its toxin to sedges. Thus, an important aspect of the subject invention concerns a novel method for selective and species-specific control of sedges. Specifically, a phytotoxin, or mixture of phytotoxins is delivered to the vascular tissue of these weeds. In a preferred embodiment of the subject invention, the spores or hyphae of *D. higginsii* (Luttrell) M. B. Ellis can be applied directly to the sedges. This fungus produces a phytotoxin which controls the sedges. This phytotoxin enters the vascular tissue of the sedge and causes foliar wilt and mortality. This effect can be enhanced by mechanical disruption of the plant's vascular system caused by the growth of the fungus.

One of the reasons mentioned for the success of sedges as invasive pest plant species was the apparent lack of mortality-inducing natural enemies. Sedges have not been reported previously in the literature to be colonized by microorganisms which effectively lead to death.

The use of this novel fungus to administer species-specific control of sedges is a highly advantageous means of reducing host populations. One of the primary advantages of using this effective microbial herbicide is the avoidance of pesticidal contamination of agricultural lands, waterways, and wetlands.

The phytotoxic composition of the subject invention can be delivered to the target pest by allowing *D. higginsii* (Luttrell) M. B. Ellis to grow directly on the weed. Advantageously, the phytotoxic composition is most effectively introduced onto the plant using standard agricultural carriers for this type of microbial herbicide.

The *D. higginsii* isolate did not cause any symptoms on members of the Poaceae family or on the crop plants tested. It was pathogenic to purple nutsedge, yellow nutsedge, annual sedge, globe sedge, and rice flatsedge. All these sedges are important weeds in different crops and turf. Inoculum formulated in N-GEL (Hercules, inc., Wilmington, Del.) or METAMUCIL (Procter & Gamble, Cincinnati, Ohio) is highly effective in killing purple nutsedge. *Dactylaria higginsii* not only reduced the shoot number and the tuber dry weight of purple nutsedge, it also appears to be able to reduce the competition imposed by purple nutsedge at the critical crop-growing period as shown by the early development of disease symptoms and the rapid rate of disease progress.

A subculture of the novel fungus has been deposited in the permanent collection of the American Type Culture Collection(ATCC), 12301 Parklawn Drive, Rockville, Md. 20852 USA on August 7, 1996. The culture was assigned the accession number ATCC 74379 by the repository.

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of a deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of a deposit. All restrictions on the availability to the public of the subject culture deposit will be irrevocably removed upon the granting of a patent disclosing it.

The fungus of the subject invention can be grown on solid or in liquid media. Solid media that can be used include water agar, potato dextrose agar, V-8 agar, and string bean agar (strained extract of macerated string beans solidified in agar). Spores are produced on solid V-8 medium exposed to fluorescent light. Specifically, solid media can be, for example, (1) water agar, (2) potato dextrose agar (Difco), (3) lima bean agar (Difco), (4) corn meal agar (Difco), (5) potato-carrot agar (Tuite 19), and (6) Desmodium agar (blend 10 g Desmodium plant parts or plant extracts in 1000 ml water and solidify with 20 g agar).

For large scale production in fermentation tanks, a liquid medium is used, for example:

TABLE 1

| Formula I: - Modified Richard's Solution - V-8* | |
| --- | --- |
| Sucrose | 50 g |
| Potassium nitrate | 10 g |
| Potassium phosphate, monobasic | 5.0 g |
| Magnesium sulfate.7H$_2$O | 2.50 g |
| Ferric chloride | 0.02 g |

TABLE 1-continued

| Formula I: - Modified Richard's Solution - V-8* | |
| --- | --- |
| V-8 juice | 15 ml |
| Distilled water to make | 1000 ml |

*Trademark, The Campbell Soup Company for mixed vegetable juices.

Formula II: Modified Richard's Solution-Distillers Solubles. Same as Formula I above but substitute 15 g Distillers solubles for V-8 juice.

Formula III: Modified Richard's Solution-Brewers yeast. Same as Formula I above but substitute 15 g brewers yeast for V-8 juice.

Formula IV: Modified Richard's Solution-Torula Yeast. Same as Formula I above but substitute 16 g torula yeast for V-8 juice.

Formula V: Oatmeal solution-4%+2% sugar. 40 g oatmeal; 20 g sucrose; 1000 ml distilled water.

The preparation of spores is commenced in preseed liter flasks containing about 300 ml of liquid medium which have been inoculated with spores. The medium is incubated for 1–3 days with agitation at a temperature of about 26° C. to about 30° C.

The preseed is then transferred aseptically to 20 liter seed tanks with additional sterile medium as described above. The tanks are provided with sterile air and agitation. The cycle is continued at a temperature of about 26° C. to about 30° C. for 1 to 3 days.

Larger fermentors (250 liter) are aseptically inoculated with the seed tanks (entire contents), described above. Additional sterile medium, as used above, is added and the pH adjusted to about 6.0. The fermentor is supplied with sterile air and agitation, and is maintained at a temperature of about 26° C. to about 30° C. for from 1 to 3 days. The fermented culture is then harvested by filtering the contents to remove insoluble solids and mycelial growth. The filtered beer is then centrifuged, the supernatant is discarded, and the remaining spore concentrate is collected, placed in plastic bags, and stored in ice. The concentrate so stored maintains an 80% germination for up to 21 days.

The spore concentrate is mixed with an agriculturally acceptable diluent or carrier for application to the undesired host vegetation or a situs. By the term "situs" is meant those areas infested with the undesired vegetation or potential infestation sites.

The preferred carrier is water, and the spore concentrate is dispersed to make a concentration of from about $1 \times 10^4$ to $1 \times 10^6$ spores/ml. The formulation is then sprayed on the undesired vegetation or situs by conventional spraying equipment in an amount of from about 50 to 500 liters per hectare.

Following are examples which illustrate procedures, including the best mode, for practicing the invention. These examples should not be construed as limiting. All percentages are by weight and all solvent mixture proportions are by volume unless otherwise noted.

EXAMPLE 1

Activity of *Dactylaria higginsii*

The host range of *D. higginsii* (ATCC 74379) was determined by inoculating various members of the Cyperaceae, the Poaceae, and members of crop species that are commonly affected by purple nutsedge (Table 2 and Table 3). For the inoculation-rate study, six levels of the inoculum were used; $1\times10^2$, $1\times10^3$; $1\times10^4$; $1\times10^5$; $1\times10^6$, and $1\times10^7$ conidia per ml. Plants were inoculated by spraying the conidial suspension onto the leaf blades until runoff. The controls were sprayed with 0.02% SILWET. The plants were then placed in a dew chamber in darkness at 28° C. for 12 hours and then transferred to greenhouse benches. Plants were examined for symptoms every 24 hours for 30 days. Infections were evaluated visually as disease severity and disease incidence based on Horsfall-Barratt scale. The experiments were replicated thrice and repeated at least twice.

A species of *Dactylaria higginsii* (Luttrell) M. B. Ellis was consistently isolated from the diseased tissues. Inoculated plants developed tiny, dark-brown flecks on the leaves four days after inoculation. The lesions enlarged to form elliptical, pale-brown spots surrounded by a narrow, dark-brown border. Under greenhouse conditions a gray, velvety layer of conidiophores and conidia developed on both surfaces of the lesions. The spots coalesced to form larger irregular spots and blotches, and the leaves died back from the tips, partially killing most of the leaves. The mycelium grew internally in the infected tissue. The conidiophores emerged through the epidermal cells, either singly or in small clusters. The conidiophores were inflated at the base and tapered toward the apex; they were 0–1 septate and hyaline. At the apex, a crown of 2–4 dactyliform denticles were formed on which the conidia were borne. The conidiophores were often proliferous, producing 2–3 successive whorls of conidia. They were 37.4–55 μm long, 4.4–8.6 μm at the base, 3.5–5.0 μm, at the middle, and 2.0–2.7 μm at the apex. The conidia were hyaline, obclavate, usually 2-septate (rarely 1-septate), not constricted at the septum, smooth, and had thin walls. A protuberance at the basal end marked the point of attachment to the conidiophore. The conidia measured 22.2–33.6×5.3–6.7 μm, mean 28.6×6.5 μm, and the length/width ratio was 4.4.

The host reaction to *D. higginsii* was determined from the disease severity on test plants classified on the basis of the infection types: 0=no visible reaction; 1=minute, pinhead sized spots; 2=small brown to dark brown lesions with no distinguishable centers; 3=small eyespot-shapedlesions with gray centers; and 4=typical coalescing lesions, elliptical with gray centers. Lesion type 0, 1, and 2 were regarded as resistant host reactions; lesion types 3 and 4 were considered susceptible, since conidia were recovered from these lesions after incubation. The reactions of various members of the tested plants are shown in Tables 2 and 3.

*Dactylaria higginsii* was very pathogenic to yellow nutsedge (*C. esculentus* L.), annual sedge (*C. compressus* L.), globe sedge (*C. globulosus* Aublet), and rice flatsedge (*C. iria* L.) as indicated by infection type 3 and 4 (Table 2). All of these are weeds in different situations such as row crops, vegetables, and lawns. Inoculation with *D. higginsii* caused severe infection on purple nutsedge 25 days after inoculation and significantly reduced the shoot number, shoot dry weight, and tuber dry weight by as much as 73%, 71%, and 67% respectively (FIG. 1).

The results of the host-range study confirmed that *D. higginsii* was nonpathogenic to members of the Poaceae and the crops species tested as indicated by the disease incidence "0" and infection type "0" (Table 3).

*Dactylaria higginsii* can also kill and control *Kyllinga brevifolia*, which is an important weed in turfgrass, golf courses, and other situations. Thus, the control of this weed, which is also known as *Cyperus brevifolius*, is economically important to the turfgrass and golf course operations.

TABLE 2

Disease incidence and disease rating of plants in the Cyperaceae family that were inoculated with *D. higginsii*

|  | Disease incidence | Infection type[1] |
|---|---|---|
| *Cyperus rotundus* | | |
| Gainesville, FL | 100 | 4 |
| Puerto Rico | 100 | 4 |
| Virgin Island | 100 | 4 |
| *C. esculentus* | | |
| Gainesville, FL | 100 | 4 |
| South Carolina | 100 | 3 |
| Maryland | 100 | 4 |
| Hood River, OR | 80 | 3 |
| Ohio | 100 | 4 |
| Pennsylvania | 100 | 4 |
| Franklin, MI | 100 | 4 |
| Mesa, WA | 100 | 4 |
| Frankfurt, KY | 85 | 3 |
| Oklahoma | 100 | 4 |
| Greenfield, CA | 100 | 4 |
| Texas | 100 | 4 |
| *C. compressus* | 95 | 3 |
| *C. globulosus* | 90 | 3 |
| *C. iria* | 85 | 3 |
| *C. papyrus* | 0 | 0 |
| *C. surinamensis* | 0 | 0 |
| *Carex fisca* | 0 | 0 |
| *Psilocarva nitens* | 0 | 0 |

[1]Infection score: 0 = no infection; 1 = minute, pinhead sized spots; 2 = small brown to dark brown lesions with no distinguishable center; 3 = small eyespot-shaped lesions with gray center; 4 = typical blast lesions, elliptical with gray center usually coalescing.

TABLE 3

Disease incidence and infection type of plants inoculated with *Dactylaria higginsii*

| Host | Disease Incidence | Infection Type* |
|---|---|---|
| *Avena sativa* L. | 0 | 0 |
| *Sorghum vulgare* Pers. | 0 | 0 |
| *Eleusine indica* L. | 0 | 0 |
| *Hordeum vulgare* L. | 0 | 0 |
| *Triticum aestivum* L. | 0 | 0 |
| *Lolium perenne* L. | 0 | 0 |
| *Oryza sativa* L. | 0 | 0 |
| *Panicum maximum* L. | 0 | 0 |
| *Echinocloa crusgalli* Beauv. | 0 | 0 |
| *Setaria faberii* Herm. | 0 | 0 |
| *Paspalum notatum* Flugge | 0 | 0 |
| *Digitaria horizontalis* Willd. | 0 | 0 |
| *Digitaria sanguinalis* (L.) Scop. | 0 | 0 |
| *Cenchrus echinatus* L. | 0 | 0 |
| *Zea mays* L. | 0 | 0 |
| *Zizania aquatica* L. | 0 | 0 |
| *Daucus carota* L. var. *sativa* (Hoffm.) | 0 | 0 |
| *Brassica oleraceae* L. | 0 | 0 |
| *Glycine max* (L.) Merr. | 0 | 0 |
| *Pisum sativum* L. | 0 | 0 |
| *Lycopersicum esculentum* L. | 0 | 0 |
| *Solanum tuberosum* L. | 0 | 0 |
| *Curcubit pepo* L. | 0 | 0 |
| *Capsicum annum* L. | 0 | 0 |
| *Saccharum officinarum* L. | 0 | 0 |
| *Musa sp.* | 0 | 0 |

*Infection score: 0 = no infection; 1 = minute, pinhead-sized spots; 2 = small brown to dark brown lesions with no distinguishable centers; 3 = small eyespot-shaped lesions with grey centers; 4 = typical blast lesions, elliptical with grey centers usually coalescing.

Figure 2:
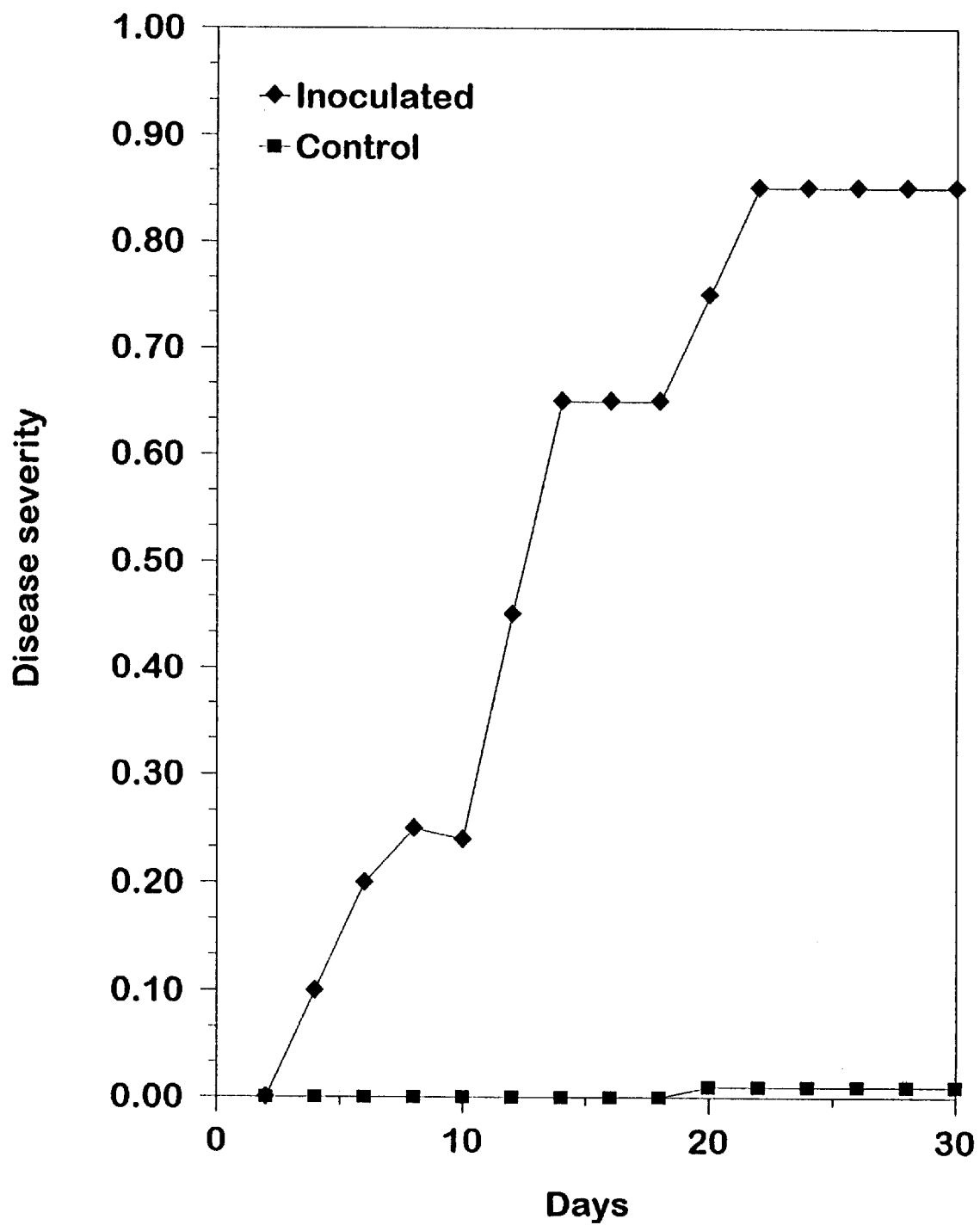
FIG. 2 shows the effect of *D. higginsii* on the disease progress curve of dactylaria leaf spot of purple nutsedge.

The disease progress on purple nutsedge as measured by disease severity is shown in FIG. 2. The fungus had a latent period of 4 days and the infection rate of 0.23. Under greenhouse conditions there were secondary infections 20 days after inoculation (FIG. 2).

EXAMPLE 2

Effect of Various Inoculum Levels

Figure 3:
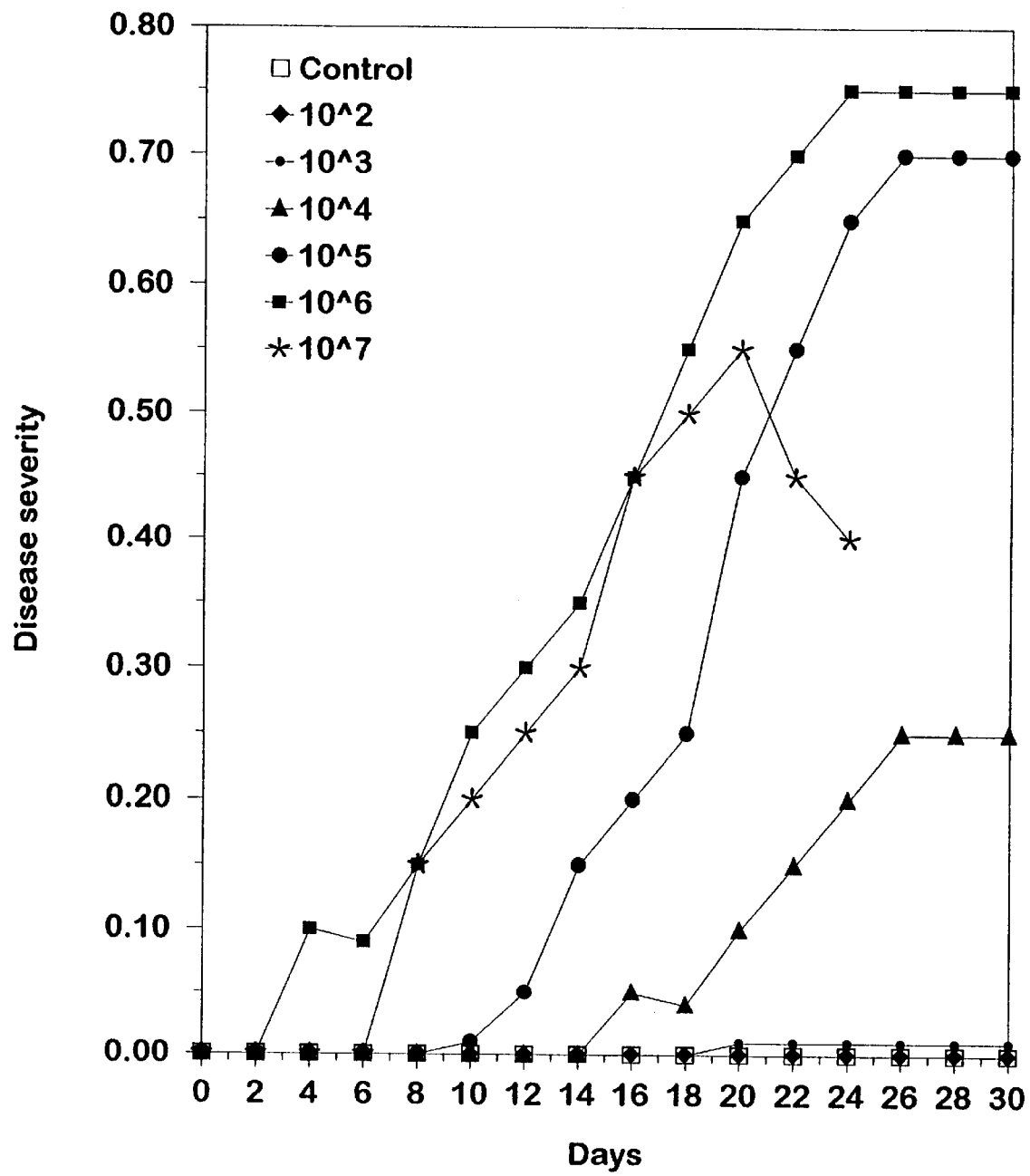
FIG. 3 shows the effect of inoculum level on the disease progress curve of dactylaria leaf spot of purple nutsedge.

The effect of various inoculum levels on the disease progress is indicated by FIG. 3. Disease severity reached the maximum (about 75%) at about 24 days when plants were inoculated with $1 \times 10^6$ conidia per ml, and the symptoms appeared 4 days after inoculation. When the inoculum level was increased to $1 \times 10^7$ conidia per ml, the maximum disease severity was 55% but dropped off 16 days after inoculation. The latent period was delayed to about 6 days. When the plants were inoculated with $1 \times 10^5$ spores per ml, the maximum disease of about 70% developed 24 days after inoculation and the latent period was delayed to about 10 days. Lower levels of disease developed for the low inoculum levels; the lowest infective inoculum level was $1 \times 10^4$. At this level not only was the disease development reduced, it was also delayed until 16 days after inoculation (FIG. 3).

EXAMPLE 3

Use of Amendments

Figure 4:
FIG. 4 shows the effect of amendments on the efficacy of *Dactylaria higginsii*.

Different amendments were tested for their ability to promote infection, disease development, and nutsedge control. The experiment was conducted in the greenhouse using $1 \times 10^6$ conidia per ml of water and the amendments listed in Table 4. Based on the ability of the amendment treatment to promote spore germination, disease incidence, and disease severity, 0.02% METAMUCIL and 0.05% N-gel were rated the best material to formulate the inoculum of *D. higginsii* for bioherbicidal use. FIG. 4 illustrates the ability to kill purple nutsedge plants with formulations containing N-GEL and METAMUCIL compared to a treatment with conidia plus silwet or treatments without the amendment (conidia only) and a control (no fungus).

TABLE 4

Effect of amendments to *Dactylaria higginsii* conidia on spore germination and disease development

|  | Spore Germination (Percentage) | Number of Lesions/Leaf | Number of Infected Leaves/Plant | Disease Incidence (Percentage) | Disease Severity (Proportion) |
| --- | --- | --- | --- | --- | --- |
| SILWET | 64.25 | 22.25 | 3.75 | 63.50 | 0.59 |
| TRITON X-100 | 63.75 | 9.80 | 3.00 | 57.50 | 0.40 |
| METAMUCIL | 93.00 | 36.00 | 6.00 | 100 | 0.95 |
| N-GEL | 92.75 | 37.75 | 6.00 | 100 | 0.87 |
| KELZAN | 96.00 | 26.65 | 5.50 | 95.50 | 0.85 |
| NATROSOL | 96.00 | 25.80 | 2.50 | 76.80 | 0.58 |
| SILWET + METAMUCIL | 91.50 | 33.00 | 5.60 | 86.75 | 0.90 |
| SILWET + N-GEL | 96.50 | 25.50 | 2.60 | 85.00 | 0.25 |
| SILWET + KELZAN | 94.00 | 20.50 | 3.80 | 85.00 | 0.20 |
| CONTROL (H2O) | 27.00 | 4.25 | 3.25 | 16.25 | 0.05 |

The following commercial products were used at the rates given in parentheses:
SILWET L-77 (0.02% v/v), a trademark of OSi Corporation has the chemical name of polyaklyleneoxide modified heptamethyltrisiloxane, in the chemical family of silicone-polyether copolymer. It is obtained from Lovland Industries, Greely, CO.
TRITON X-100 (0.05% v/v) (a registered trademark of Union Carbide Chemicals & Plstics Co., Inc.) has the chemical name of t-occylphenoxypolyethoxyethanol. It is a nonionic surfactant in the chemical family of polyoxyethylene ethers and is obtained from Sigma Chemical Company, St. Louis, MO.
METAMUCIL (0.05% w/v) (regular, unflavored), a trademark of Procter & Gamble, Cincinnati, OH, is a plant-derived polysaccharide in the chemical family of hydrophilic mucilloid, available in most drugstores and supermarkets in the United States.
N-GEL (0.05% w/v), a trademark of Hercules Inc., Wilmington, DE, is a nonionic derivative of cellulose.
KELZAN S (0.05% w/v), a registered product of the Kelco Division of Merck & Co., is a xanthan gum, derived from the exocellular mucilaginous material produced by the common bacteria belonging to the genus Xanthomonas.
NATROSOL (0.05% w/v), a registered product of Aqualon Company, Wilmington, DE, is a nonionic hydroxyethylcellulose.

EXAMPLE 4

Combinations of Herbicidal Agents

One embodiment of the subject invention concerns the combination of the isolate with a mycoherbicide for nutsedge control. Our novel fungal isolate can also be combined with the isolates of rust for control of yellow nutsedge. Spores of the novel fungus can also be mixed with spores of other bioherbicides to enlarge the scope of control of undesired vegetation. For example, a mixture of the novel *D. higginsii* with *Alternaria cassiae* can be used to control both yellow and purple nutsedge and sicklepod (*Cassia obtusifolia*). Further, spores of the novel *D. higginsii* can be mixed with those of *A. cassiae* to control yellow and purple nutsedge and showy crotalaria or coffee senna. The use of *A. cassiae* to control sicklepod, showy crotalaria, and coffee senna is disclosed in U.S. Pat. No. 4,390,360, which is incorporated herein by reference thereto. The culture, means of growing, and application to these weeds disclosed in U.S. Pat. No. 4,390,360 can be used herein. Mixtures of *D. higginsii* and *A. cassiae*, for example, *A. cassiae* NRRL 12533, can be made by methods well known in the art, utilizing the disclosure of U.S. Pat. No. 4,390,360, and that contained herein.

The novel *D. higginsii* of the subject invention can also be mixed, in an agricultural carrier, with the rust pathogen *Puccinia canaliculata*. *P. canaliculata* has been reported to control yellow nutsedge and the mixture can be used to control both purple and yellow nutsedges. The novel *D. higginsii* described here can also be mixed with *Colletotrichum dematium* (Schw.) Andrus & Moore, having the identifying characteristics of NRRL 15933, and is used to control Florida beggarweed as described in U.S. Pat. No. 4,643,756, issued to Cardina et al. This mixture could be used to control both purple nutsedge and Florida beggarweed.

The effectiveness of the novel D. higginsii may also be enhanced by mixing it with chemical herbicides such as 2, 4-D, atrazine, linuron, paraquat, alachlor, metolachlor, glyphosate, dichlobenil, EPTC, and arsenicals.

Table 5 provides a list of other groups of herbicides which could be used in conjunction with the novel fungus of the subject invention.

TABLE 5

| Herbicide group | Example |
| --- | --- |
| Carbamate | dichlobenil |
| Thiocarbamate | EPTC |
| Substituted urea | linuron |
| Triazine | atrazine |
| Asymmetrical triazine | metribuzin |
| Substituted uracil | terbacil |
| Chloroacetamide | metolachlor |
| Acid amide | pronamide |
| Bipyridinium | paraquat |
| Sulfonyl urea | chlorsulfuron |
| Imidazolinone | imazaquin |
| Dinitroaniline | trifluralin |
| Diphenyl ethers | oxyfluorfen |
| Difenoxycarboxylic acid | fluazifop |
| Benzoic acid | amiben |
| Phenoxy | 2,4-D |
| Unclassed | glyphosate |

Though spores are the preferred form of the fungus, the fungus can also be used in its vegetative form. For example, fragmented mycelia can be formulated and applied to purple nutsedge in much the same manner as described above for the spore form.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A process for controlling *Cyperus brevifolius*, said process comprising the application of an agricultural composition comprising an isolate of the fungus *Dactylaria higginsii* having the identifying characteristics of ATCC 74379.

2. The process, according to claim 1, wherein said fungus is in the spore form at a concentration of from about $1 \times 10^4$ spores/ml of carrier to about $1 \times 10^9$ spores/ml of carrier.

3. The process, according to claim 1, which further comprises application of a chemical herbicide.

* * * * *

UNITED STATES PATENT AND TRADEMARK OFFICE
CERTIFICATE OF CORRECTION

PATENT NO.   : 5,945,378

DATED        : August 31, 1999

INVENTOR(S)  : Jugah Kadir, Raghavan Charudattan

It is certified that error appears in the above-identified patent and that said Letters Patent is hereby corrected as shown below:

Column 2, line 23: "flumigants" should read --fumigants--.

Column 4, line 9: "brevzfolia" should read --brevifolia--.

Column 5, line 14: "Collection(ATCC)" should read --Collection (ATCC)--.

Signed and Sealed this

Twenty-second Day of February, 2000

Attest:

Q. TODD DICKINSON

Attesting Officer

Commissioner of Patents and Trademarks